(12) United States Patent
Banning et al.

(10) Patent No.: US 8,841,472 B2
(45) Date of Patent: Sep. 23, 2014

(54) COLORED POLYSILOXANES

(75) Inventors: Jeffery H Banning, Hillsboro, OR (US);
James D Padgett, Lake Oswego, OR (US); Michael J Edwards, Beaverton, OR (US); Stephan V Drappel, Toronto (CA); Joseph B Gault, West Linn, OR (US)

(73) Assignee: Xerox Corporation, Norwalk, CT (US)

( * ) Notice: Subject to any disclaimer, the term of this patent is extended or adjusted under 35 U.S.C. 154(b) by 83 days.

(21) Appl. No.: 13/323,747

(22) Filed: Dec. 12, 2011

(65) Prior Publication Data

US 2013/0150571 A1 Jun. 13, 2013

(51) Int. Cl.
*C07F 7/08* (2006.01)

(52) U.S. Cl.
USPC ......................................... 556/405

(58) Field of Classification Search
USPC ......................................... 556/405
See application file for complete search history.

(56) References Cited

U.S. PATENT DOCUMENTS

| 8,456,733 B2 * | 6/2013 | Fontana et al. | 359/296 |
| 2005/0008588 A1 * | 1/2005 | Candau et al. | 424/59 |

* cited by examiner

*Primary Examiner* — Brian McDowell
(74) *Attorney, Agent, or Firm* — Shimokaji & Associates

(57) ABSTRACT

Disclosed are compounds of the formulae

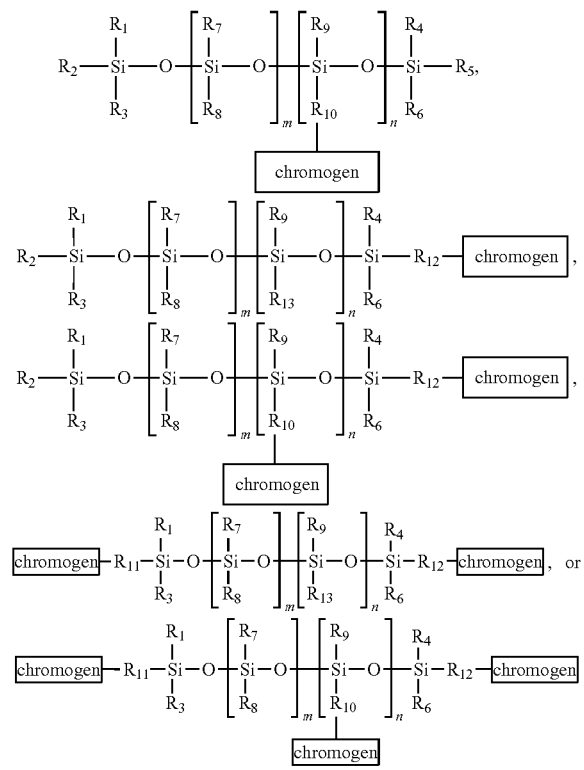

wherein $R_1$, $R_2$, $R_3$, $R_4$, $R_5$, $R_6$, $R_7$, $R_8$, $R_9$, and $R_{13}$ are hydrogen, alkyl, aryl, arylalkyl, or alkylaryl, $R_{10}$, $R_{11}$, and $R_{12}$ are alkylene, arylene, arylalkylene, or alkylarylene, and the chromogen moiety is an atom or group of atoms that impart color to the compound in the visible, infrared, or ultraviolet wavelength range.

4 Claims, No Drawings

COLORED POLYSILOXANES

BACKGROUND

Disclosed herein is a colored polysiloxane composition. More specifically, disclosed herein are polysiloxanes having chromogens covalently bonded thereto.

Polysiloxanes such as polydimethylsiloxane (PDMS) are used as release fluids for phase change hot melt ink printers. These materials are also used for a variety of other applications, such as release agents in electrophotographic fusing. Many people are also familiar with PDMS because it is a component in SILLY PUTTY, to which PDMS imparts its characteristic viscoelastic properties. The rubbery, vinegary-smelling silicone caulks, adhesives, and aquarium sealants are also well-known PDMS-containing materials. PDMS is further used as a component in silicone grease and other silicone-based lubricants, as well as in defoaming agents, mold release agents, damping fluids, heat transfer fluids, polishes, cosmetics, hair conditioners, and other applications. With proper crosslinking, elastomeric material for gaskets or the like can also be made.

Often it is desirable to "follow" the "progress" of the polysiloxane as it works its way throughout the printing process. Because of the unique solubility parameters of polysiloxanes, however, it is extremely difficult if not impossible to dissolve a dye in these materials.

Accordingly, while known materials are suitable for their intended purposes, a need remains for methods for following the progress of polysiloxanes as these materials pass through a machine. In addition, a need remains for "colored" polysiloxanes, whether the "color" be in the visible wavelength range or detectable in the UV or IR or some other wavelength range not visible to the human eye. Further, a need remains for methods of synthesizing compounds which comprise a chromogen covalently bound to a polysiloxane while dealing with the difficulties inherent in the insolubility of dyes and other materials in polysiloxanes.

SUMMARY

Disclosed herein is a compound of the formula

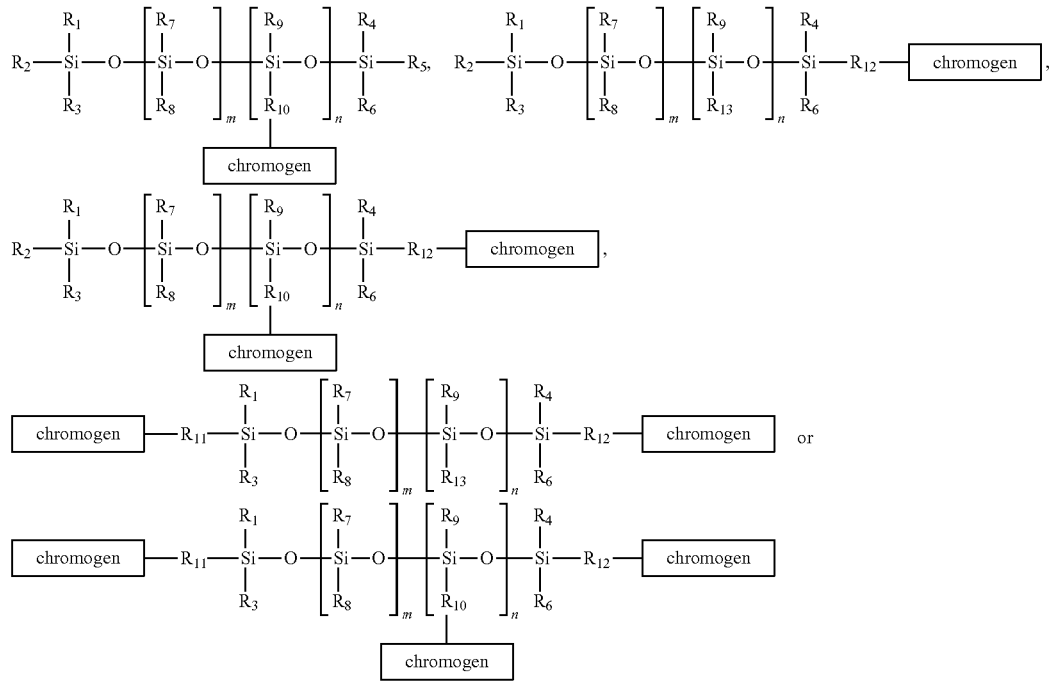

wherein $R_1$, $R_2$, $R_3$, $R_4$, $R_5$, $R_6$, $R_7$, $R_8$, $R_9$, and $R_{13}$ each, independently of the others, are: (i) hydrogen atoms; (ii) alkyl groups, including substituted and unsubstituted alkyl groups, wherein hetero atoms may optionally be present in the alkyl group; (iii) aryl groups, including substituted and unsubstituted aryl groups, wherein hetero atoms may optionally be present in the aryl group; (iv) arylalkyl groups, including substituted and unsubstituted arylalkyl groups, wherein hetero atoms may optionally be present in either the aryl or the alkyl of the arylalkyl group; or (v) alkylaryl groups, including substituted and unsubstituted alkylaryl groups, wherein hetero atoms may optionally be present in either the aryl or the alkyl portion of the alkylaryl group; wherein $R_{10}$, $R_{11}$, and $R_{12}$ each, independently of the others, are: (i) alkylene groups, including substituted and unsubstituted alkylene groups, wherein hetero atoms may optionally be present in the alkylene group; (ii) arylene groups, including substituted and unsubstituted arylene groups, wherein hetero atoms may optionally be present in the arylene group; (iii) arylalkylene groups, including substituted and unsubstituted arylalkylene groups, wherein hetero atoms may optionally be present in either the aryl or the alkyl of the arylalkylene group; or (iv) alkylarylene groups, including substituted and unsubstituted alkylarylene groups, wherein hetero atoms may optionally be present in either the aryl or the alkyl portion of the alkylarylene group; and wherein the chromogen moiety is an atom or group of atoms that impart color to the compound in the visible, infrared, or ultraviolet wavelength range.

DETAILED DESCRIPTION

Disclosed herein are compounds of the formula

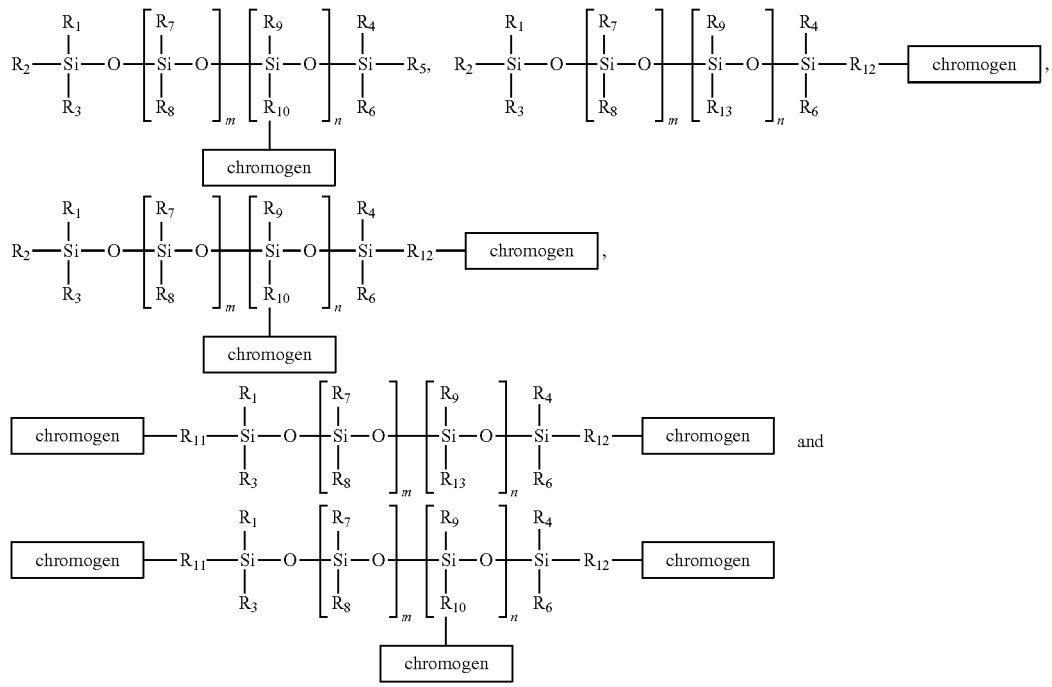

wherein:

$R_1$, $R_2$, $R_3$, $R_4$, $R_5$, $R_6$, $R_7$, $R_8$, $R_9$, and $R_{13}$ each, independently of the others, are:

(i) hydrogen atoms;

(ii) alkyl groups (including linear and branched, saturated or unsaturated, cyclic and acyclic, and substituted and unsubstituted alkyl groups, wherein hetero atoms, such as oxygen, nitrogen, sulfur, silicon, phosphorus, boron, or the like, may optionally be present in the alkyl group, in one embodiment with at least about 1 carbon atom, and in one embodiment with no more than about 22 carbon atoms, and in another embodiment with no more than about 5 carbon atoms, although the number of carbon atoms can be outside of these ranges;

(iii) aryl groups (including substituted and unsubstituted aryl groups, wherein hetero atoms, such as oxygen, nitrogen, sulfur, silicon, phosphorus, boron, or the like, may optionally be present in the aryl group, in one embodiment with at least about 6 carbon atoms, and in one embodiment with no more than about 12 carbon atoms, although the number of carbon atoms can be outside of these ranges;

(iv) arylalkyl groups (including substituted and unsubstituted arylalkyl groups, wherein the alkyl portion of the arylalkyl group can be linear or branched, saturated or unsaturated, cyclic or acyclic, and substituted or unsubstituted, and wherein hetero atoms, such as oxygen, nitrogen, sulfur, silicon, phosphorus, boron, or the like, may optionally be present in either the aryl or the alkyl of the arylalkyl group), in one embodiment with at least about 7 carbon atoms, and in one embodiment with no more than about 28 carbon atoms, in another embodiment with no more than about 10 carbon atoms, although the number of carbon atoms can be outside of these ranges, such as benzyl or the like; or (v) alkylaryl groups (including substituted and unsubstituted alkylaryl groups, wherein the alkyl portion of the alkylaryl group can be linear or branched, saturated or unsaturated, cyclic or acyclic, and substituted or unsubstituted, and wherein hetero atoms, such as oxygen, nitrogen, sulfur, silicon, phosphorus, boron, or the like, may optionally be present in either the aryl or the alkyl portion of the alkylaryl group, in one embodiment with at least about 7 carbon atoms, and in one embodiment with no more than about 28 carbon atoms, in another embodiment with no more than about 10 carbon atoms, although the number of carbon atoms can be outside of these ranges, such as such as tolyl or the like;

and wherein $R_{10}$, $R_{11}$, and $R_{12}$ each, independently of the others, are:

(i) alkylene groups (including linear and branched, saturated or unsaturated, cyclic and acyclic, and substituted and unsubstituted alkylene groups, wherein hetero atoms, such as oxygen, nitrogen, sulfur, silicon, phosphorus, boron, or the like, may optionally be present in the alkylene group, in one embodiment with at least about 1 carbon atom, and in one embodiment with no more than about 22 carbon atoms, and in another embodiment with no more than about 5 carbon atoms, although the number of carbon atoms can be outside of these ranges;

(ii) arylene groups (including substituted and unsubstituted arylene groups, wherein hetero atoms, such as oxygen, nitrogen, sulfur, silicon, phosphorus, boron, or the like, may optionally be present in the arylene group, in one embodiment with at least about 6 carbon atoms, and in one embodiment with no more than about 12 carbon atoms, although the number of carbon atoms can be outside of these ranges;

(iii) arylalkylene groups (including substituted and unsubstituted arylalkylene groups, wherein the alkyl portion of the arylalkylene group can be linear or branched, saturated or unsaturated, cyclic or acyclic, and substituted or unsubstituted, and wherein hetero atoms, such as oxygen, nitrogen, sulfur, silicon, phosphorus, boron, or the like, may optionally be present in either the aryl or the alkyl of the arylalkylene group), in one embodiment with at least about 7 carbon atoms, and in one embodiment with no more than about 28 carbon atoms, in another embodiment with no more than about 10 carbon atoms, although the number of carbon atoms can be outside of these ranges, such as benzylene or the like; or (iv) alkylarylene groups (including substituted and unsubstituted alkylarylene groups, wherein the alkyl portion of the alkylarylene group can be linear or branched, saturated or unsaturated, cyclic or acyclic, and substituted or unsubstituted, and wherein hetero atoms, such as oxygen, nitrogen, sulfur, silicon, phosphorus, boron, or the like, may optionally be present in either the aryl or the alkyl portion of the alkylarylene group, in one embodiment with at least about 7 carbon atoms, and in one embodiment with no more than about 28 carbon atoms, in another embodiment with no more than about 10 carbon atoms, although the number of carbon atoms can be outside of these ranges, such as such as tolylene or the like; and wherein the chromogen moiety is an atom or group of atoms that impart color to the compound in the visible, infrared, or ultraviolet wavelength range;

wherein the substituents on the substituted alkyl, alkylene, aryl, arylene, arylalkyl, arylalkylene, alkylaryl, and alkylarylene groups can be, but are not limited to, halogen atoms, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, mixtures thereof, or the like, wherein two or more substituents can be joined together to form a ring.

In some embodiments, mixtures of two or more monomers are included in the chromogen-unsubstituted group "m". In some embodiments, mixtures of two or more monomers are included in the chromogen-substituted group "n".

In one specific embodiment, $R_1$, $R_2$, $R_3$, $R_4$, $R_5$, $R_6$, $R_7$, $R_8$, $R_9$, and $R_{13}$ are all methyl groups.

In one specific embodiment, at least one of $R_{10}$, $R_{11}$, and $R_{12}$ is an n-propylene group. In another specific embodiment, at least one of $R_{10}$, $R_{11}$, and $R_{12}$ is an n-ethylene group.

For the purposes of the discussion herein, the term "chromogen" will be used to refer both to groups of atoms that impart color to a molecule and to molecules that are colored. By "color" and "colored" is meant that the molecule absorbs light in the visible, ultraviolet, or infrared wavelength range. A "chromogenic compound" is a compound that, whether or not it is itself colored, is capable of reacting with a polysiloxane compound to produce a polysiloxane having chromogen moieties covalently bonded thereto.

For purposes of the present discussion, "visible wavelength range" is defined as from about 400 to about 700 nanometers; "ultraviolet wavelength range" is defined as from about 200 to about 400 nanometers; and "infrared wavelength range" is defined as from about 700 to about 1,400 nanometers.

In one embodiment, the chromogen moiety is an anthraquinone moiety. The anthraquinone moiety can be of the formula

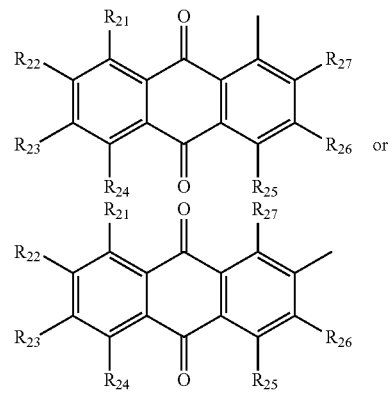

wherein:

$R_{21}$, $R_{22}$, $R_{23}$, $R_{24}$, $R_{25}$, $R_{26}$, and $R_{27}$ each, independently of the others, can be:

(i) hydrogen atoms;

(ii) alkyl groups (including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group), in one embodiment with at least 1 carbon atom, and in one embodiment with no more than about 50 carbon atoms, in another embodiment with no more than about 30 carbon atoms, and in yet another embodiment with no more than about 18 carbon atoms, although the number of carbon atoms can be outside of these ranges;

(iii) aryl groups (including unsubstituted and substituted aryl groups, and wherein hetero atoms, such as oxygen, nitrogen, sulfur, silicon, phosphorus, boron, or the like either may or may not be present in the aryl group), in one embodiment with at least about 6 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges;

(iv) arylalkyl groups (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as benzyl or the like;

(v) alkylaryl groups (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as tolyl or the like;

(vi) halogen atoms, such as fluorine, chlorine, bromine, iodine, or the like;

(vii) ester groups;

(viii) amide groups;

(ix) sulfone groups;

(x) amine or ammonium groups;

(xi) nitrile groups;

(xii) nitro groups;

(xiii) hydroxy groups;

(xiv) mercapto (thiol) groups;

(xv) cyano groups;

(xvi) pyridine or pyridinium groups;

(xvii) ether groups;

(xviii) thioether groups;

(xix) aldehyde groups;

(xx) ketone groups;

(xxi) carbonyl groups;

(xxii) thiocarbonyl groups;

(xxiii) sulfate groups;

(xxiv) sulfide groups;

(xxv) sulfoxide groups;

(xxvi) phosphine or phosphonium groups;

(xxvii) phosphate groups;

(xxviii) nitroso groups;

(xxix) acyl groups;

(xxx) acid anhydride groups;

(xxxi) azide groups;

(xxxii) azo groups;

(xxxiii) cyanato groups;

(xxxiv) isocyanato groups;

(xxxv) thiocyanato groups;

(xxxvi) isothiocyanato groups;

(xxxvii) urethane (carbamate) groups;

(xxxviii) urea (carbamide) groups;

(xxxix) carboxylic acid or carboxylate groups; or (xl) sulfonic acid or sulfonate groups;

wherein $R_{21}$, $R_{22}$, $R_{23}$, $R_{24}$, $R_{25}$, $R_{26}$, and $R_{27}$ can each be joined to a ring in the central structure;

wherein two or more of $R_{21}$, $R_{22}$, $R_{23}$, $R_{24}$, $R_{25}$, $R_{26}$, and $R_{27}$ can be joined together to form a ring;

wherein examples of the substituents on the substituted alkyl, aryl, arylalkyl, and alkylaryl groups include (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring.

In one specific embodiment, the chromogen moiety is of the formula

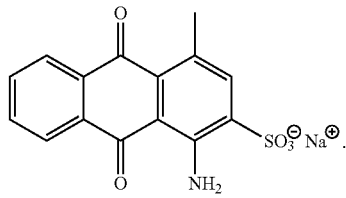

In another specific embodiment, the chromogen moiety is of the formula

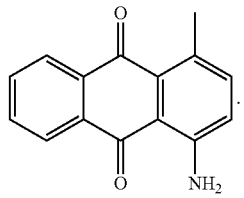 [SMILES: Cc1ccc(N)c2c1C(=O)c1ccccc1C2=O]

Anthraquinone chromogens can be reacted with the polysiloxane by any desired or effective method. In one embodiment, the reaction proceeds as follows:

An amine-functionalized polysiloxane, such as one of the general formula

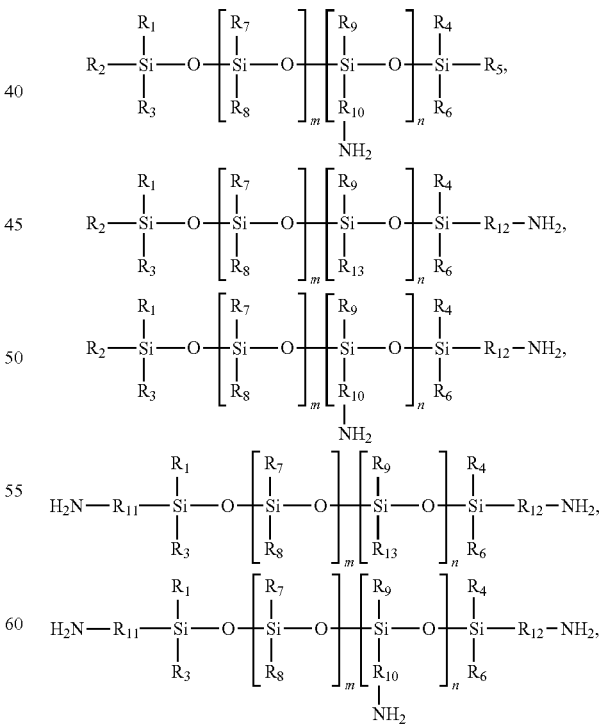

or mixture thereof can be reacted with an anthraquinone dye having thereon a substituent reactive to amines, such as a halogen atom or the like, in the presence of a copper adduct catalyst, such as copper acetate, copper metal powder, copper sulfate, or other copper salts, as well as mixtures thereof, and a solvent in which the ingredients are soluble or miscible, such as tetrahydrofuran, a mixture of water and tetrahydrofuran, or the like, in the presence of heat and stirring, to form the product. Secondary amines can also be employed.

The reaction between the amine-functionalized polysiloxane and the brominated anthraquinone can take place at any desired or suitable temperature, in one embodiment at least about 25° C., in another embodiment at least about 50° C., and in yet another embodiment at least about 75° C., and in one embodiment no more than about 150° C., in another embodiment no more than about 125° C., and in yet another embodiment no more than about 100° C., although the temperature can be outside of these ranges.

The reaction between the amine-functionalized polysiloxane and the brominated anthraquinone can take place for any desired or effective period of time, in one embodiment at least about 30 minutes, in another embodiment at least about 1 hour, and in yet another embodiment at least about 5 hours, and in one embodiment no more than about 1 week, in another embodiment no more than about 4 days, and in yet another embodiment no more than about 1 day, although the time period can be outside of these ranges.

The relative amount of amine-functionalized polysiloxane to amine-reactive anthraquinone can be any desired or effective molar ratio, in one embodiment at least about 1:0.05, in another embodiment at least about 1:0.5, and in yet another embodiment at least about 1:0.9, and in one embodiment no more than about 1:1.05, in another embodiment no more than about 1:1.01, and in yet another embodiment no more than about 1:1, although the relative amounts can be outside of these ranges.

The amount of copper adduct catalyst present can be any desired or effective amount, in one embodiment at least about in one embodiment in a molar ratio with respect to the dye of at least about 1:1000, in another embodiment at least about 1:500, and in yet another embodiment at least about 1:100, and in one embodiment no more than about 1:1, in another embodiment no more than about 1:5, and in yet another embodiment no more than about 1:50, although the amount can be outside of these ranges.

The relative amount of solvent present with respect to siloxane by weight can be any desired or effective amount, in one embodiment at least about 1:100, in another embodiment at least about 1:50, and in yet another embodiment at least about 1:2, and in one embodiment no more than about 1:1, in another embodiment no more than about 5:1, and in yet another embodiment no more than about 25:1, although the amount can be outside of these ranges.

The relative amount of tetrahydrofuran to water can be any desired or relative ratio, in one embodiment at least about 1000:1, in another embodiment at least about 500:1, and in yet another embodiment at least about 100:1, and in one embodiment no more than about 1:1, in another embodiment no more than about 5:1, and in yet another embodiment no more than about 25:1, although the relative amounts can be outside of these ranges.

In another embodiment, the chromogen moiety is a phthalocyanine moiety. The phthalocyanine moiety can be of the formula

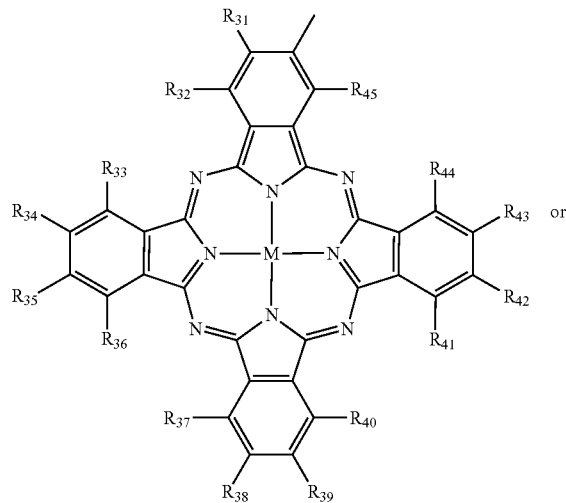

or

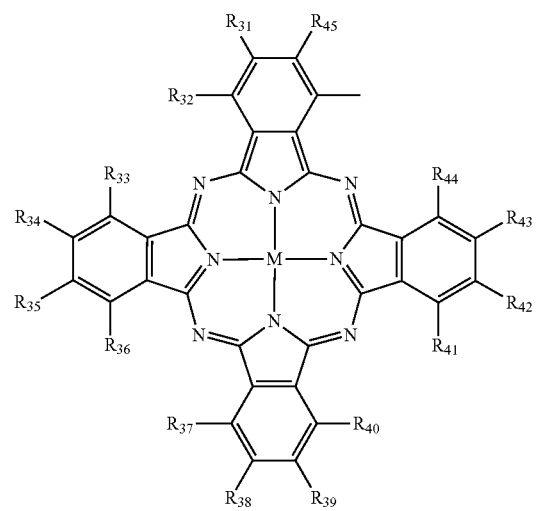

wherein:

$R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, and $R_{45}$ each, independently of the others, can be:
(i) hydrogen atoms;
(ii) alkyl groups (including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group), in one embodiment with at least 1 carbon atom, and in one embodiment with no more than about 50 carbon atoms, in another embodiment with no more than about 30 carbon atoms, and in yet another embodiment with no more than about 18 carbon atoms, although the number of carbon atoms can be outside of these ranges;
(iii) aryl groups (including unsubstituted and substituted aryl groups, and wherein hetero atoms, such as oxygen, nitrogen, sulfur, silicon, phosphorus, boron, or the like either may or may not be present in the aryl group), in one embodiment with at least about 6 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges;

(iv) arylalkyl groups (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as benzyl or the like;

(v) alkylaryl groups (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as tolyl or the like;

(vi) halogen atoms, such as fluorine, chlorine, bromine, iodine, or the like;

(vii) ester groups;

(viii) amide groups;

(ix) sulfone groups;

(x) amine or ammonium groups;

(xi) nitrile groups;

(xii) nitro groups;

(xiii) hydroxy groups;

(xiv) mercapto (thiol) groups;

(xv) cyano groups;

(xvi) pyridine or pyridinium groups;

(xvii) ether groups;

(xviii) thioether groups;

(xix) aldehyde groups;

(xx) ketone groups;

(xxi) carbonyl groups;

(xxii) thiocarbonyl groups;

(xxiii) sulfate groups;

(xxiv) sulfide groups;

(xxv) sulfoxide groups;

(xxvi) phosphine or phosphonium groups;

(xxvii) phosphate groups;

(xxviii) nitroso groups;

(xxix) acyl groups;

(xxx) acid anhydride groups;

(xxxi) azide groups;

(xxxii) azo groups;

(xxxiii) cyanato groups;

(xxxiv) isocyanato groups;

(xxxv) thiocyanato groups;

(xxxvi) isothiocyanato groups;

(xxxvii) urethane (carbamate) groups;

(xxxviii) urea (carbamide) groups;

(xxxix) carboxylic acid or carboxylate groups; or (xl) sulfonic acid or sulfonate groups;

wherein $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, and $R_{45}$ can each be joined to a ring in the central structure;

wherein two or more of $R_{31}$, $R_{32}$, $R_{33}$, $R_{34}$, $R_{35}$, $R_{36}$, $R_{37}$, $R_{38}$, $R_{39}$, $R_{40}$, $R_{41}$, $R_{42}$, $R_{43}$, $R_{44}$, and $R_{45}$ can be joined together to form a ring;

wherein examples of the substituents on the substituted alkyl, aryl, arylalkyl, and alkylaryl groups include (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring;

and M is an atom or group of atoms capable of bonding to the central cavity of a phthalocyanine molecule, wherein axial ligands optionally can be attached to M. About seventy atoms or groups are known to bond in the central cavity of a phthalocyanine molecule, as disclosed in, for example, *Phthalocyanine Materials*, N. B. McKeown, Cambridge University Press (1998), Chapter 1, Table 1.1, the disclosure of which is totally incorporated herein by reference, including, but not limited to, two hydrogen, lithium, sodium, or potassium atoms; a divalent metal atom, such as beryllium, magnesium, calcium, strontium, barium, chromium, manganese, iron, cobalt, nickel, copper, zinc, tin, lead, cadmium, or the like, as well as mixtures thereof; a divalent halometal or -metalloid group, such as chloroiron(III), chlorotitanium(III), chlorochromium(III), chloroaluminum, chlorogallium, chloroindium, chlorophosphorus(III), dichlorotitanium(IV), dichlorosilicon, dichlorogermanium, dichlorotin, or the like, as well as the corresponding fluorides, bromides, and iodides and mixtures thereof; a divalent hydroxy metal group, such as hydroxyaluminum, hydroxygallium, dihydroxysilicon, dihydroxygermanium, dihydroxytin, or the like as well as mixtures thereof; a divalent oxo-metal group, such as oxo-molybdenum(IV), oxo-vanadium(IV), oxo-titanium(IV), or the like as well as mixtures thereof; a divalent metal- or metalloidal-oxyhydrocarbon group, such as alkoxyaluminum, alkoxygallium, dialkoxysilicon, diaryloxygermanium, or the like as well as mixtures thereof, wherein the oxyhydrocarbon group is an oxyalkyl group, an oxyaryl group, an oxyalkylaryl group, an oxyarylalkyl group, an oxyheterocyclic group, or mixtures thereof, and typically (although not necessarily) contains from one to about twenty carbon atoms; or the like, as well as mixtures thereof.

In one specific embodiment, the chromogen moiety is copper phthalocyanine, of the formula

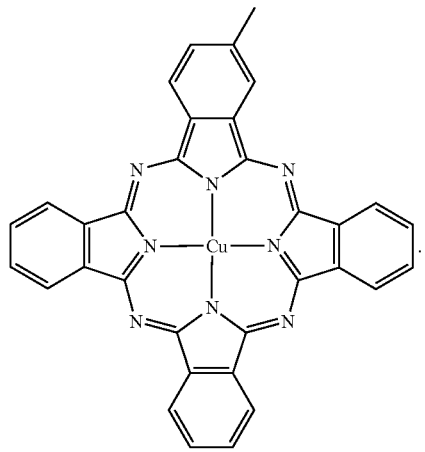

Phthalocyanine chromogens can be reacted with the polysiloxane by any desired or effective method. In one embodiment, the reaction proceeds as follows.

A mercapto-functionalized (thiol-functionalized) polysiloxane, of the general formula

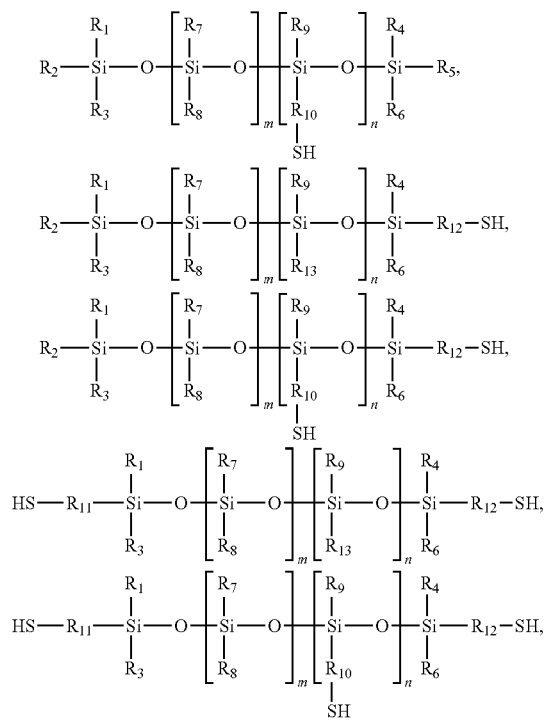

or mixture thereof is reacted with a phthalonitrile synthon with a leaving group, such as nitrophthalonitrile, naphthalene dicarbonitrile, or the like, as well as mixtures thereof, in the presence of a base, such as $K_2CO_3$, $Na_2CO_3$, $Li2CO_3$, NaOH, KOH, LiH, NaH, KH, Hunig's base, other tertiary amines, or the like, as well as mixtures thereof, and a polar aprotic solvent, such as dimethylformamide or the like, as well as mixtures thereof, with heat and stirring, to form a phthalocyanine precursor derivatized polysiloxane. Thereafter, the phthalocyanine precursor derivatized polysiloxane is reacted with a phthalonitrile synthon in excess (to minimize "crosslinking" of the polysiloxane chains through the phthalocyanine groups) in the presence of a metal salt, such as anhydrous and hydrated salts or complexes of the formula $$MX_n \cdot yH_2O$$

wherein M is a metal, such as lithium, sodium, potassium, beryllium, magnesium, calcium, scandium, titanium, zirconium, vanadium, niobium, chromium, molybdenum, manganese, rhenium, iron, ruthenium, cobalt, rhodium, nickel, palladium, platinum, copper, zinc, cadmium, aluminum, gallium, indium, silicon, germanium, tin, lead, or the like, as well as mixtures thereof, X is an anion, such as a carboxylate-containing moiety, such as formate, acetate, acetoacetate, propionate, butyrate, benzoate, or the like, as well as mixtures thereof, an alkoxide, such as methoxide, ethoxide, isopropoxide, or the like, as well as mixtures thereof, acetyl acetonate, a halide atom, such as fluoride, chloride, bromide, or iodide, as well as mixtures thereof, sulfate, alkyl sulfonate, aryl sulfonate, nitrate, nitrite, phosphate, or the like, as well as mixtures thereof, n is a number representing the valence of the metal, and y is an integer of from 0 to about 10. Specific examples include (but are not limited to) anhydrous copper chloride, hydrated copper chloride, anhydrous copper acetate, hydrated copper acetate, anhydrous copper sulfate, hydrated copper sulfate, anhydrous copper nitrate, hydrated copper nitrate, anhydrous copper bromide, hydrated copper bromide, or the like, as well as mixtures thereof. The reagents are mixed in the presence of a solvent, such as ethylene glycol, amyl alcohol, hexanol, heptanol, tetralin, decalin, ISOPAR® (refined mineral spirits solvents available from Exxon), xylene, tributyl amine, N,N-dimethylaniline, quinoline, 1-chloronaphthalene, trialkanolamines, monoalkyl dialkanolamines, dialkyl monoalkanolamines (such as 2-dimethylaminoethanol, 2-diethylaminoethanol, 2-dimethylamino-1-propanol, or the like), dimethylsulfoxide, N,N-dimethylformamide, N,N-dimethylacetamide, 1-methyl-2-pyrrolidinone, N-cyclohexyl-2-pyrrolidinone, sulfolane, or the like, as well as mixtures thereof, with heat and stirring to form the phthalocyanine-derivatized polysiloxane product.

The relative amount of metal salt to phthalonitrile synthon can be any desired or effective molar ratio, in one embodiment at least about 1:3, in another embodiment at least about 1:3.5, and in yet another embodiment at least about 1:4, and in one embodiment no more than about 1:5, in another embodiment no more than about 1:4.5, and in yet another embodiment no more than about 1:4.1, although the relative amounts can be outside of these ranges.

The relative amount of mercapto-functionalized polysiloxane to phthalonitrile synthon can be any desired or effective molar ratio, in one embodiment at least about 1:0.1, in another embodiment at least about 1:0.2, and in yet another embodiment at least about 1:0.9, and in one embodiment no more than about 1:1, in another embodiment no more than about 1:1.05, and in yet another embodiment no more than about 1:1.01, although the relative amounts can be outside of these ranges.

The relative amount of base to phthalonitrile synthon can be any desired or effective molar ratio, in one embodiment at least about 1:10, in another embodiment at least about 1:5, and in yet another embodiment at least about 1:1, and in one embodiment no more than about 1.1:1, in another embodiment no more than about 1.5:1, and in yet another embodiment no more than about 2:1, although the amount can be outside of these ranges.

The relative amount of solvent to siloxane by weight for the formation of the precursor can be any desired or relative ratio, in one embodiment at least about 1:100, in another embodiment at least about 1:50, and in yet another embodiment at least about 1:2, and in one embodiment no more than about 1:1, in another embodiment no more than about 5:1, and in yet another embodiment no more than about 25:1, although the amount can be outside of these ranges.

Formation of the precursor can take place at any desired or suitable temperature, in one embodiment at least about 25° C., in another embodiment at least about 50° C., and in yet another embodiment at least about 75° C., and in one embodiment no more than about 150° C., in another embodiment no more than about 125° C., and in yet another embodiment no more than about 100° C., although the temperature can be outside of these ranges.

Formation of the precursor can take place for any desired or effective period of time, in one embodiment at least about 30 minutes, in another embodiment at least about 1 hour, and in yet another embodiment at least about 5 hours, and in one embodiment no more than about 1 week, in another embodiment no more than about 4 days, and in yet another embodiment no more than about 1 day, although the time period can be outside of these ranges.

The phthalocyanine precursor derivatized polysiloxane and the phthalonitrile are present in relative amounts such that the phthalonitrile is present in an excess amount, to avoid "crosslinking" of polysiloxane chains through the phthalocyanine groups thus formed, as follows:

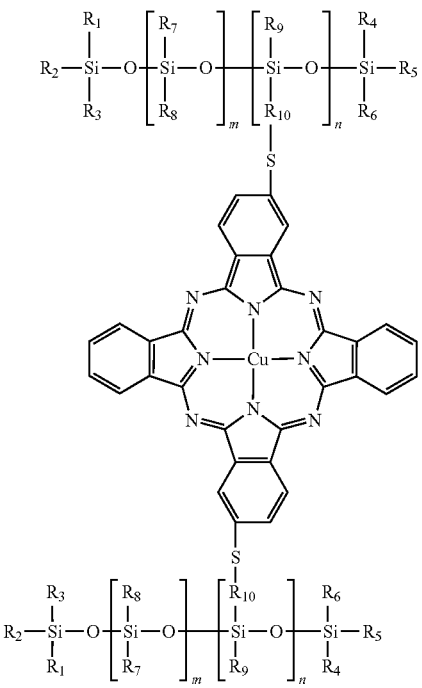

unless such crosslinking is in fact desired. The relative amount of phthalocyanine precursor derivatized polysiloxane to phthalonitrile can be any desired or effective molar ratio, in one embodiment at least about 1:3, in another embodiment at least about 1:4, and in yet another embodiment at least about 1:5, and in one embodiment no more than about 1:20, in another embodiment no more than about 1:15, and in yet another embodiment no more than about 1:10, although the relative amounts can be outside of these ranges.

The metal salt is present in any desired or effective molar amount with respect to the phthalonitrile, in one embodiment at least about 1:5, in another embodiment at least about 1:4, and in yet another embodiment at least about 1:3, and in one embodiment no more than about 1:10, in another embodiment no more than about 1:7, and in yet another embodiment no more than about 1:6, although the amount can be outside of these ranges.

The relative amount of solvent with respect to the siloxane by weight for the formation of the final phthalocyanine-substituted polysiloxane product can be any desired or effective ratio, in one embodiment at least about 1:100, in another embodiment at least 1:50, and in yet another embodiment at least 1:2, and in one embodiment no more than about 1:1, in another embodiment no more than about 5:1, and in yet another embodiment no more than about 25:1, although the amount can be outside of these ranges.

The reaction between the precursor and the phthalonitrile can take place at any desired or suitable temperature, in one embodiment at least about 50° C., in another embodiment at least about 75° C., and in yet another embodiment at least about 100° C., and in one embodiment no more than about 200° C., in another embodiment no more than about 175° C., and in yet another embodiment no more than about 150° C., although the temperature can be outside of these ranges.

The reaction between the precursor and the phthalonitrile can take place for any desired or effective period of time, in one embodiment at least about 1 hour, in another embodiment at least about 6 hours, and in yet another embodiment at least about 12 hours, and in one embodiment no more than about 6 days, in another embodiment no more than about 2 days, and in yet another embodiment no more than about 1 day, although the time period can be outside of these ranges.

In yet another embodiment, the chromogen moiety is a rhodamine moiety. The rhodamine moiety can be of the formula

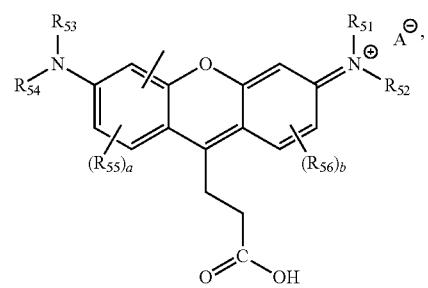

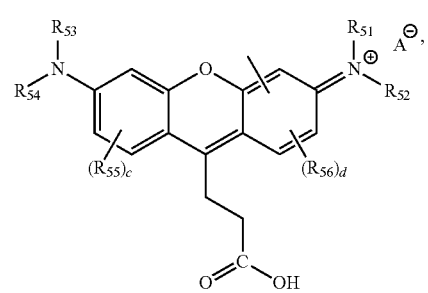

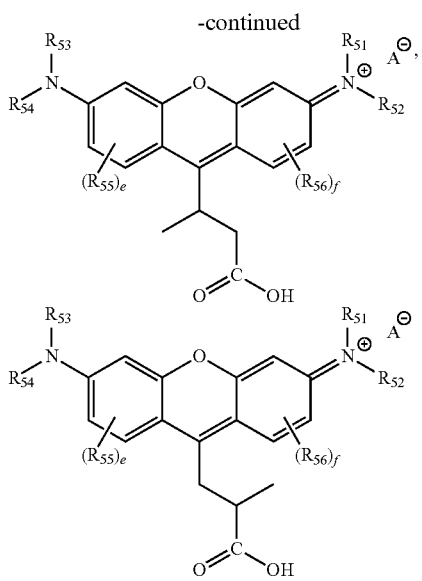

wherein:

$R_{51}$, $R_{52}$, $R_{53}$, and $R_{54}$ each, independently of the others, can be:
(i) hydrogen atoms;
(ii) alkyl groups (including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group), in one embodiment with at least 1 carbon atom, and in one embodiment with no more than about 55 carbon atoms, in another embodiment with no more than about 30 carbon atoms, and in yet another embodiment with no more than about 20 carbon atoms, although the number of carbon atoms can be outside of these ranges;
(iii) aryl groups (including unsubstituted and substituted aryl groups, and wherein hetero atoms, such as oxygen, nitrogen, sulfur, silicon, phosphorus, boron, or the like either may or may not be present in the aryl group), in one embodiment with at least about 5 carbon atoms, and in another embodiment with at least about 6 carbon atoms, and in one embodiment with no more than about 26 carbon atoms, in another embodiment with no more than about 22 carbon atoms, and in yet another embodiment with no more than about 18 carbon atoms, although the number of carbon atoms can be outside of these ranges;
(iv) arylalkyl groups (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group), in one embodiment with at least about 6 carbon atoms, and in another embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as benzyl or the like; or
(v) alkylaryl groups (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group), in one embodiment with at least about 6 carbon atoms, and in another embodiment with at least about 7 carbon atoms, and in one embodiment with no more than about 55 carbon atoms, in another embodiment with no more than about 30 carbon atoms, and in yet another embodiment with no more than about 20 carbon atoms, although the number of carbon atoms can be outside of these ranges, such as tolyl or the like;

wherein $R_{51}$ and $R_{52}$ can be joined together to form a ring, wherein $R_{53}$ and $R_{54}$ can be joined together to form a ring, and wherein $R_{51}$, $R_{52}$, $R_{53}$, and $R_{54}$ can each be joined to a phenyl ring in the central structure;

a and d each, independently of the other, is an integer which is 0, 1, or 2;

b, c, e, and f each, independently of the others, is an integer which is 0, 1, 2, or 3;

each of $R_{55}$ and $R_{56}$, independently of the others can be:
(i) alkyl groups (including linear, branched, saturated, unsaturated, cyclic, substituted, and unsubstituted alkyl groups, and wherein hetero atoms, such as oxygen, nitrogen, sulfur, silicon, phosphorus, boron, or the like either may or may not be present in the alkyl group), in one embodiment with at least 1 carbon atom, and in one embodiment with no more than about 50 carbon atoms, in another embodiment with no more than about 30 carbon atoms, and in yet another embodiment with no more than about 18 carbon atoms, although the number of carbon atoms can be outside of these ranges;
(ii) aryl groups (including unsubstituted and substituted aryl groups, and wherein hetero atoms, such as oxygen, nitrogen, sulfur, silicon, phosphorus, boron, or the like either may or may not be present in the aryl group), in one embodiment with at least about 6 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges;
(iii) arylalkyl groups (including unsubstituted and substituted arylalkyl groups, wherein the alkyl portion of the arylalkyl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the arylalkyl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as benzyl or the like;
(iv) alkylaryl groups (including unsubstituted and substituted alkylaryl groups, wherein the alkyl portion of the alkylaryl group can be linear, branched, saturated, unsaturated, and/or cyclic, and wherein hetero atoms, such as oxygen, nitrogen, sulfur, silicon, phosphorus, boron, or the like either may or may not be present in either or both of the alkyl portion and the aryl portion of the alkylaryl group), in one embodiment with at least about 7 carbon atoms, and in one embodiment with no more than about 55 carbon atoms, in another embodiment with no more than about 30 carbon atoms, and in yet another embodiment with no more than about 18 carbon atoms, although the number of carbon atoms can be outside of these ranges, such as tolyl or the like;
(v) halogen atoms, such as fluorine, chlorine, bromine, iodine, or the like;
(vi) ester groups;
(vii) amide groups;

(viii) sulfone groups;
(ix) amine or ammonium groups;
(x) nitrile groups;
(xi) nitro groups;
(xii) hydroxy groups;
(xiii) mercapto (thiol) groups;
(xiv) cyano groups;
(xv) pyridine or pyridinium groups;
(xvi) ether groups;
(xvii) thioether groups;
(xviii) aldehyde groups;
(xix) ketone groups;
(xx) carbonyl groups;
(xxi) thiocarbonyl groups;
(xxii) sulfate groups;
(xxiii) sulfide groups;
(xxiv) sulfoxide groups;
(xxv) phosphine or phosphonium groups;
(xxvi) phosphate groups;
(xxvii) nitroso groups;
(xxviii) acyl groups;
(xxix) acid anhydride groups;
(xxx) azide groups;
(xxxi) azo groups;
(xxxii) cyanato groups;
(xxxiii) isocyanato groups;
(xxxiv) thiocyanato groups;
(xxxv) isothiocyanato groups;
(xxxvi) urethane (carbamate) groups;
(xxxvii) urea (carbamide) groups;
(xxxviii) carboxylic acid or carboxylate groups; or
(xxxix) sulfonic acid or sulfonate groups;
wherein $R_{55}$, and $R_{56}$ can each be joined to a phenyl ring in the central structure;
and A is an anion, with examples of suitable anions including (but not being limited to) Cl—, Br—, I—, $HSO_4$—, $HSO_3$—, $SO_4^{2-}$, $SO_3^{2-}$, $CH_3SO_3$—, $CH_3C_6H_4SO_3$—, $NO_3$—, HCOO—, $CH_3COO$—, $H_2PO_4$—, $HPO_4^{2-}$, SCN—, $BF_4$—, $ClO_4$—, $SSO_3$—, $PF_6$—, $SbCl_6$—, or the like, as well as mixtures thereof;

wherein examples of the substituents on the substituted alkyl, aryl, arylalkyl, and alkylaryl groups include (but are not limited to) hydroxy groups, halogen atoms, amine groups, imine groups, ammonium groups, cyano groups, pyridine groups, pyridinium groups, ether groups, aldehyde groups, ketone groups, ester groups, amide groups, carbonyl groups, thiocarbonyl groups, sulfate groups, sulfonate groups, sulfonic acid groups, sulfide groups, sulfoxide groups, phosphine groups, phosphonium groups, phosphate groups, nitrile groups, mercapto groups, nitro groups, nitroso groups, sulfone groups, acyl groups, acid anhydride groups, azide groups, azo groups, cyanato groups, isocyanato groups, thiocyanato groups, isothiocyanato groups, carboxylate groups, carboxylic acid groups, urethane groups, urea groups, silyl groups, siloxyl groups, silane groups, mixtures thereof, or the like, wherein two or more substituents can be joined together to form a ring.

For example, a succinic anhydride-substituted or -terminated polysiloxane can be converted into a rhodamine-substituted polysiloxane as follows (with the instance of the anhydride-terminated polysiloxane being illustrated):

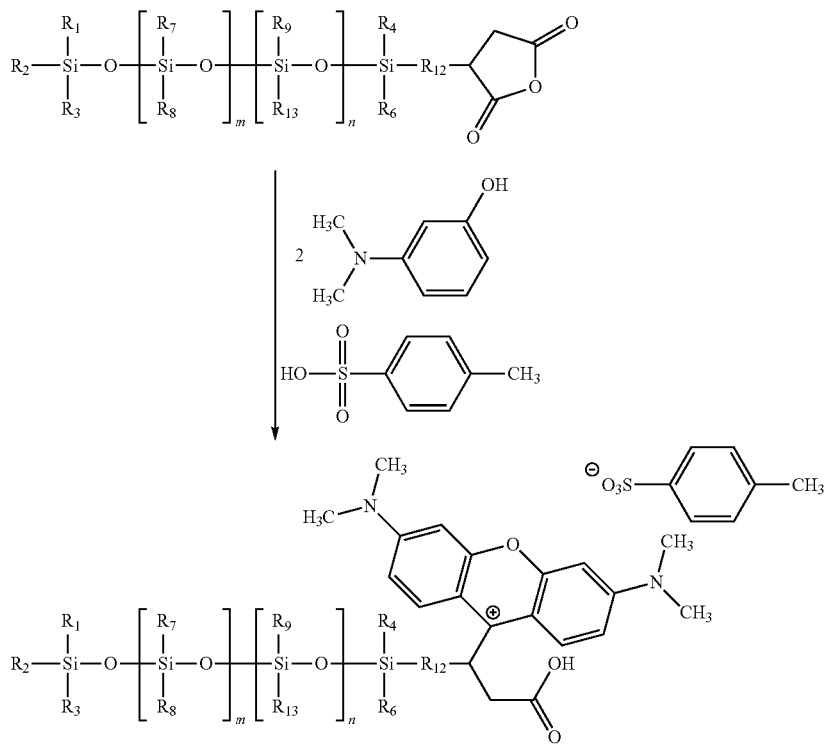

The relative amount of maleic anhydride-functionalized polysiloxane to rhodamine m-alkylamino phenol precursor can be any desired or effective molar ratio, in one embodiment at least about 1:0.25, in another embodiment at least about 1:0.75, and in yet another embodiment at least about 1:1, and in one embodiment no more than about 1:2, in another embodiment no more than about 1:1.9, and in yet another embodiment no more than about 1:1.8, although the relative amounts can be outside of these ranges.

The relative amount of solvent to siloxane by weight for the formation of the precursor can be any desired or relative ratio, in one embodiment at least about 1:100, in another embodiment at least about 1:50, and in yet another embodiment at least about 1:2, and in one embodiment no more than about 1:1, in another embodiment no more than about 5:1, and in yet another embodiment no more than about 25:1, although the amount can be outside of these ranges.

Formation of the precursor can take place at any desired or suitable temperature, in one embodiment at least about 25° C., in another embodiment at least about 50° C., and in yet another embodiment at least about 75° C., and in one embodiment no more than about 150° C., in another embodiment no more than about 125° C., and in yet another embodiment no more than about 100° C., although the temperature can be outside of these ranges.

Formation of the precursor can take place for any desired or effective period of time, in one embodiment at least about 30 minutes, in another embodiment at least about 1 hour, and in yet another embodiment at least about 5 hours, and in one embodiment no more than about 1 week, in another embodiment no more than about 4 days, and in yet another embodiment no more than about 1 day, although the time period can be outside of these ranges.

The counter anion is present in any desired or effective molar amount with respect to the rhodamine, in one embodiment at least about 1:0.1, in another embodiment at least about 1:0.5, and in yet another embodiment at least about 1:0.9, and in one embodiment no more than about 1:1, in another embodiment no more than about 1:1.05, and in yet another embodiment no more than about 1:1.1, although the amount can be outside of these ranges.

The relative amount of solvent with respect to the siloxane by weight for the formation of the final rhodamine-substituted polysiloxane product can be any desired or effective ratio, in one embodiment at least about 1:100, in another embodiment at least 1:50, and in yet another embodiment at least 1:2, and in one embodiment no more than about 1:1, in another embodiment no more than about 5:1, and in yet another embodiment no more than about 25:1, although the amount can be outside of these ranges.

The reaction between the precursor and the rhodamine can take place at any desired or suitable temperature, in one embodiment at least about 50° C., in another embodiment at least about 75° C., and in yet another embodiment at least about 100° C., and in one embodiment no more than about 200° C., in another embodiment no more than about 175° C., and in yet another embodiment no more than about 150° C., although the temperature can be outside of these ranges.

The reaction between the precursor and the rhodamine can take place for any desired or effective period of time, in one embodiment at least about 1 hour, in another embodiment at least about 6 hours, and in yet another embodiment at least about 12 hours, and in one embodiment no more than about 6 days, in another embodiment no more than about 2 days, and in yet another embodiment no more than about 1 day, although the time period can be outside of these ranges.

Other classes of chromogen moieties can also be used.

Reactive polysiloxanes can be obtained from a variety of sources, such as, for example, Gelest, Inc., Morrisville, Pa.; Shin-Etsu Chemical Company, Ltd., Tokyo, Japan; or the like.

The colorants disclosed herein can be incorporated into polysiloxane materials whenever it is desired to impart color to these materials. In addition, these colorant materials can be added to polysiloxane materials whenever it is desired to trace their progress through any process, such as a printing process or the like, when the polysiloxane material would otherwise be difficult to visualize or detect. The colorant can be added to the polysiloxane in any amount desired or effective to impart the desired degree of hue or color.

Specific embodiments will now be described in detail. These examples are intended to be illustrative, and the claims are not limited to the materials, conditions, or process parameters set forth in these embodiments. All parts and percentages are by weight unless otherwise indicated.

EXAMPLE I

To a 1 L 24/40 3-necked round-bottom flask with TEFLON-coated stir magnet and condenser was added 5.0 g 1-methylamino-2-sodium-sulfonic acid-4-bromo-anthraquinone (TCI Corp.), ~0.5 g copper II acetate, 49 g deionized water, and 350 g tetrahydrofuran (un-inhibited). The flask was placed in a 90° C. oil bath and allowed to reflux to dissolve all reactants. After ~30 min 450 g 10-15 centastoke aminopropyl-terminated polydimethylsulfoxide (PDMS) (Gelest, Inc. DMS-A11, Morrisville, Pa.) was added and allowed to stir and reflux. After 16 h the mixture was black (from a combination of the orange bromamine acid and the blue product). After ~22 h the mixture was bluish, indicating completion of the reaction and formation of the blue amine-substituted anthraquinone. After 40 h the reaction mixture was poured into a 2 L beaker with 1200 mL of methanol with stilling. After several minutes the stirring was stopped and the beaker covered with foil (to prevent evaporation) and the covalently bound dye-to-PDMS was allowed to settle. The methanol/THF was decanted and the remaining covalently bound dye-to-PDMS was placed in a 1 L 1-neck round-bottom flask and the remaining solvent was distilled off. The slightly viscous covalently bound dye-to-PDMS was poured into a jar with samples used to dilute colorless samples of PDMS. The product was believed to be of the formula

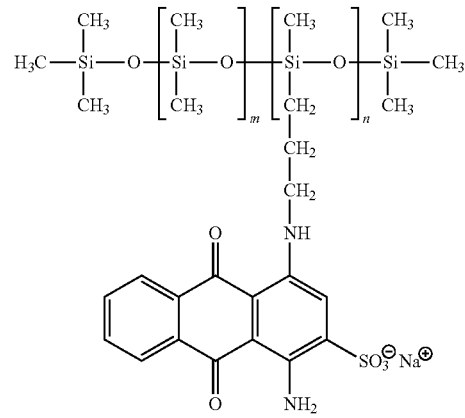

wherein the average number of —NH$_2$ groups per molecule was about 2 and the value of Mw was about 900.

EXAMPLE II

To a 1 L 24/40 3-necked round-bottom flask with TEFLON-coated stir magnet and condenser was added 5.0 g 1-methylamino-4-bromo-anthraquinone (Aceto Corp.), ~2.0 g copper II acetate tetrahydrate, 20 g deionized water, and 380 g tetrahydrofuran (un-inhibited). The flask was placed in a 90° C. oil bath and allowed to reflux to dissolve all reactants. After ~30 min 400 g 10-15 centastoke aminopropyl-terminated polydimethylsulfoxide (Gelest, Inc. DMS-A11) was added and allowed to stir and reflux. The anthraquinone starting material was red, and the desired product was blue.

After ~1 h the mixture was violet, indicating progression of the reaction. After ~22 h the mixture was royal blue, indicating completion of the reaction, and the flask removed from the oil bath. The mixture was transferred to a 2 L separatory funnel and washed 3× with 1 L of deionized water. The covalently bound dye-to-PDMS was placed in a 1 L 1-neck round-bottom flask and the remaining water was distilled off.

The slightly viscous covalently bound dye-to-PDMS was poured into a jar with samples used to dilute colorless samples of PDMS. The product was believed to be of the formula

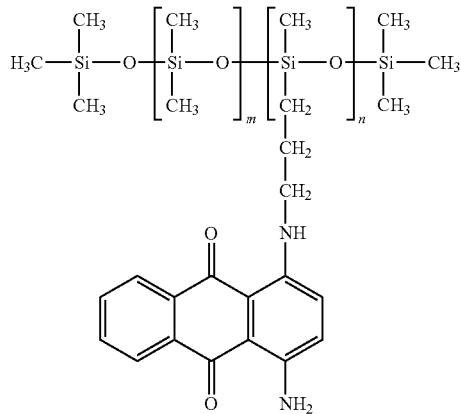

wherein the average number of —NH$_2$ groups per molecule was about 2 and the value of Mw was about 900.

EXAMPLE III

To a 100 mL 1-neck round-bottom flask equipped with TEFLON-coated magnetic stir was charged 25 g mercapto-functionalized PDMS (1% SH, MW=33 for SH; —SH makes up 1% of the molecule's molecular weight), 60 g dimethylformamide, and 1.05 g K$_2$CO$_3$. The flask was placed in a 120° C. oil bath and stirring initiated. After about 1 h, 1.44 g 4-nitrophthalonitrile was added and the reaction continued for 3 h. The reaction mixture was then quenched in about 100 mL methanol and transferred to a 1 L separatory funnel. The lower functionalized PDMS oil layer was collected and dissolved in 100 mL toluene. The toluene solution was washed with 100 mL deionized water twice. The toluene was then distilled off. The oil was then transferred back to the separatory funnel and washed with 100 mL acetone twice. The lower functionalized PDMS oil layer was collected and dried in a 90° C. vacuum oven. A phthalocyanine precursor derivatized PDMS was obtained, believed to be of the formula

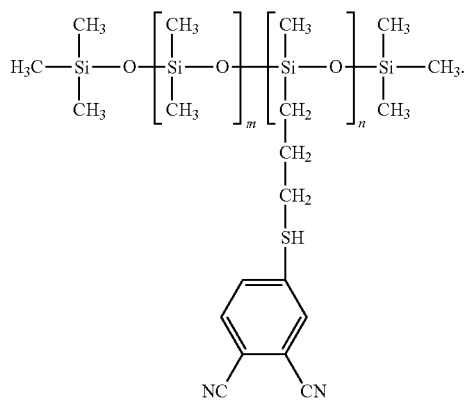

To a 250 mL 1-neck round-bottom flask equipped with TEFLON-coated magnetic stir and a condenser was charged 10 g of the precursor thus prepared, 0.56 g phthalonitrile, 0.16 g CuCl$_2$, and ~100 g hexanol. The flask was placed in a 160° C. oil bath and stirring initiated. The solution began to turn light green after the temperature of the contents of the flask reached about 160° C. The reactants appeared soluble at the beginning of the reaction, but eventually became cloudy. After 6.5 h of stirring, the reaction mixture was cooled then poured into a separatory funnel. There were three phases in the funnel: the bottom was a very light blue PDMS-oil phase, the middle was a brown rag layer with some blue solids, and the top layer was a light green hexanol phase. The lower oil phase was collected. The UV curve of PDMS-oil phase in toluene was measured. There was a peak at 672 nm and another smaller one at 350 nm. The 672 nm peak was characteristic of a phthalocyanine dye. The product was believed to be of the formula

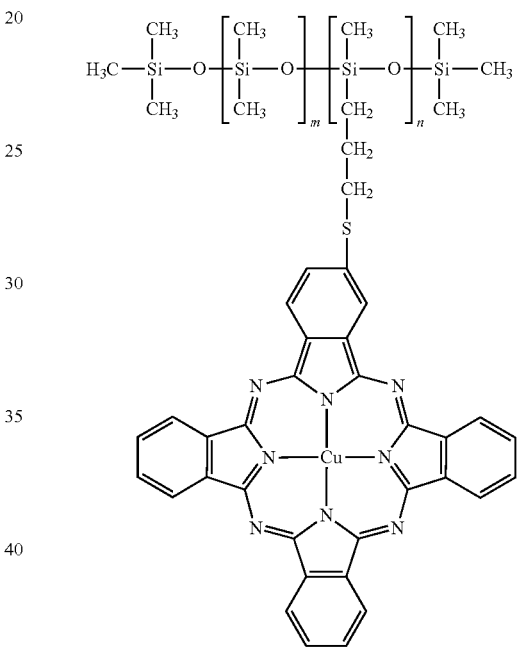

wherein the value of Mw was about 7,000 and the degree of substitution was about 1%.

EXAMPLE IV

To a 500 mL 24/40 3-necked round-bottom flask with TEFLON-coated stir magnet and condenser is added about 45.25 g 3-(dimethylamino)phenol (available from Aldrich Chemical Co., Milwaukee, Wis.) and about 100 g 75-100 centastoke succinic anhydride-terminated polydimethylsulfoxide (Mw about 800 g/mole; available as DMS-A11 from Gelest, Inc., Morrisville, Pa.). The flask is placed in a 90° C. oil bath and allowed to stir to dissolve all reactants. After 1 h the mixture is allowed to heat to 150° C. until a magenta color is formed and consistent throughout. Then about 21.5 g of p-toluenesulfonic acid (Aldrich Chemical Co.) is added and the reaction is allowed to cool to 90° C. and held for 1 h. The reaction mixture is cooled to room temperature and poured into a jar. The structure thus obtained is believed to be as follows:

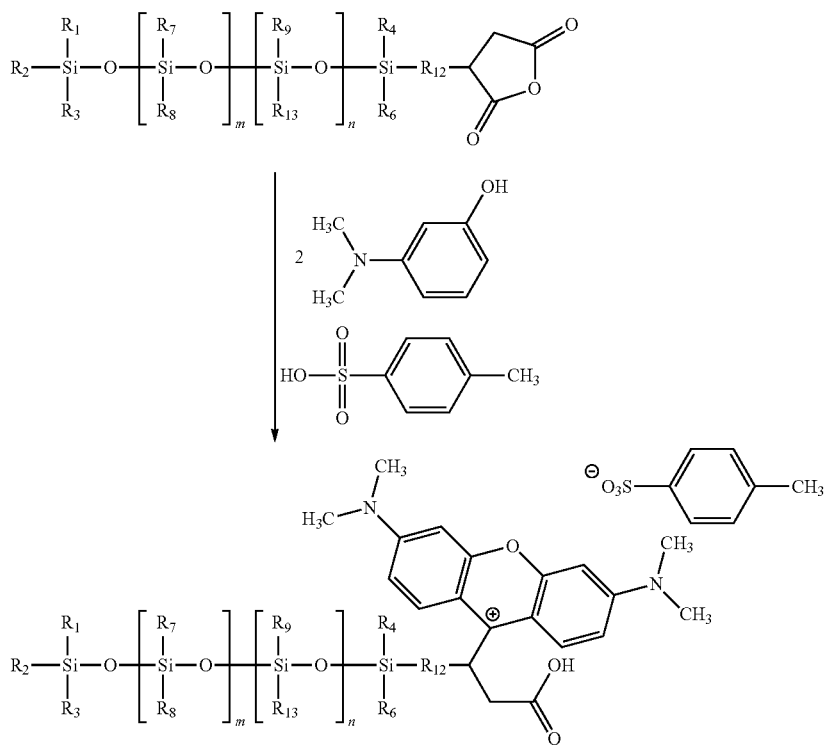

EXAMPLE V

The process of Example III is repeated except that 0.16 g $MnCl_2$ is used instead of 0.16 g $CuCl_2$. It is believed that when the lower oil phase is collected and the UV-VIS-NIR curve of the PDMS-oil phase in toluene is measured, a peak will be observed at about 725 nm. It is believed that the product will be of the formula

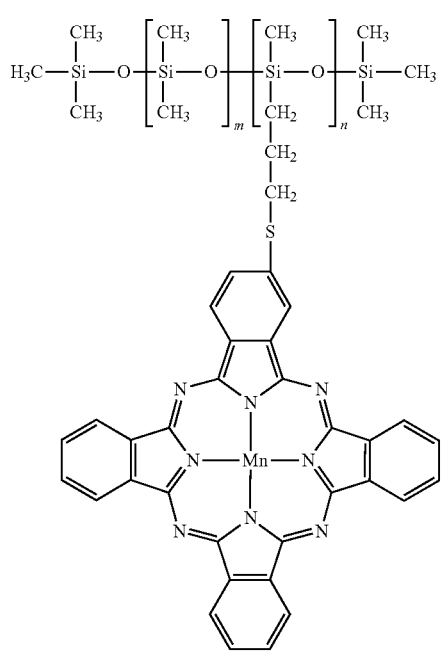

wherein the value of Mw is about 7,000 and the degree of substitution is about 1%.

EXAMPLE VI

To a 1 L 24/40 3-necked round-bottom flask with TEFLON-coated stir magnet and condenser is added 22.4 g trans-4-methoxycinnamoyl chloride (Aldrich Chemical) and 350 g tetrahydrofuran (un-inhibited). The flask is placed in a 90° C. oil bath and allowed to reflux to dissolve all reactants. After ~30 min 100 g 10-15 centastoke aminopropyl-terminated polydimethylsulfoxide (PDMS) (Gelest, Inc. DMS-A11, Morrisville, Pa.) is added and allowed to stir and reflux. After 16 h the reaction mixture is allowed to come to room temperature, and 500 mL of a 5% $Na_2CO_3$ water solution is added (to neutralize the HCl liberated during the reaction) and allowed to stir for 3 h, after which the reaction mixture is transferred to a separatory funnel. The water layer is removed and the product in THF is transferred to a distillation setup; the THF is distilled off and the product is cooled to room temperature and poured into a jar. The structure is believed to be that shown below.

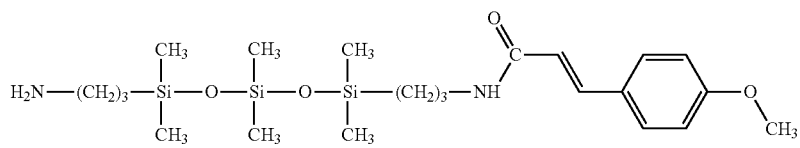

Other embodiments and modifications of the present invention may occur to those of ordinary skill in the art subsequent to a review of the information presented herein; these embodiments and modifications, as well as equivalents thereof, are also included within the scope of this invention.

The recited order of processing elements or sequences, or the use of numbers, letters, or other designations therefor, is not intended to limit a claimed process to any order except as specified in the claim itself.

What is claimed is:

1. A compound of the formula

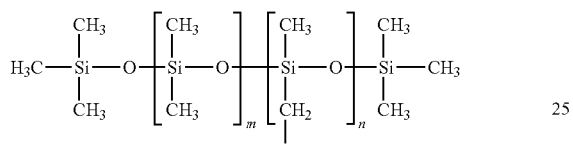

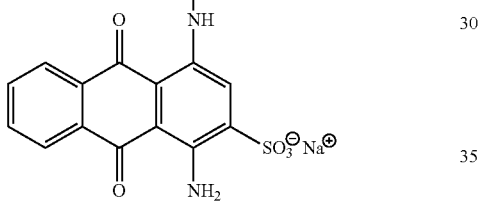

wherein "m" is two or more monomer and "n" is two or more monomers.

2. The compound of claim 1 wherein an average number of —$NH_2$ groups per molecule of the compound is about 2.

3. The compound of claim 1 having a molecular weight of 900 grams per mole.

4. The compound according to claim 1 wherein the compound is colored in the visible wavelength range.

* * * * *